United States Patent [19]
Murray

[11] Patent Number: 5,367,604
[45] Date of Patent: Nov. 22, 1994

[54] HUMIDIFIER APPARATUS AND/OR GASES DISTRIBUTION CHAMBERS AND/OR TEMPERATURE PROBE

[75] Inventor: Charles G. Murray, Auckland, New Zealand

[73] Assignee: Fisher & Paykel Limited, Auckland, New Zealand

[21] Appl. No.: 52,372

[22] Filed: Apr. 23, 1993

[30] Foreign Application Priority Data

Apr. 24, 1992 [NZ] New Zealand .............. 242484

[51] Int. Cl.⁵ .............................. F24F 6/10
[52] U.S. Cl. ..................... 392/394; 392/396
[58] Field of Search ............. 392/395, 396, 394, 402, 392/403, 405, 406; 261/141, 142, DIG. 65

[56] References Cited
U.S. PATENT DOCUMENTS 3,916,891 11/1975 Freytag .................. 392/396
4,291,838 9/1981 Williams .................. 392/394
4,910,384 3/1990 Silver .................. 392/396
5,062,145 10/1991 Zwaan .................. 392/396

*Primary Examiner*—Teresa J. Walberg
*Attorney, Agent, or Firm*—Trexler, Bushnell, Giangiorgi & Blackstone, Ltd.

[57] ABSTRACT

A humidifier provides humidified gases to a patient. The humidifier is very compact, having a gases volume of the order of 60 mls. A microporous water compartment is provided perpendicular to the gases flow to ensure efficient humidification of the gases. Also, a combined temperature probe and heater supply connector is provided which only supplies energy to the heater in the water compartment when the gases temperature sensor is appropriately positioned in the humidifier gases passageway. This reduces the risk of gases at excessively high temperatures being supplies to the patient.

53 Claims, 7 Drawing Sheets 5,367,604

HUMIDIFIER APPARATUS AND/OR GASES DISTRIBUTION CHAMBERS AND/OR TEMPERATURE PROBE

BACKGROUND OF THE INVENTION (1) Field of the Invention

This invention relates to humidifying apparatus and-/or gases distribution chambers and/or temperature probes for the same and has been devised particularly though not solely for use in providing humidified gases to a patient in a hospital in need of such humidified gases.

(2) Description of the Prior Art

Known humidification devices such as that disclosed in our U.S. Pat. No. 5,062,145 do not provide a very efficient flow path for gases passing over the microporous envelope. Also, there is no provision for providing a warning or preventing further heating of the water in the microporous envelope if one or more of the temperature sensors is removed or not inserted in the device. Furthermore, water from cooling vapour often condenses within the prior published humidification devices. This is undesirable and can be difficult to remove.

BRIEF SUMMARY OF THE INVENTION

It is an object of the present invention to provide humidifying apparatus and/or gases distribution chambers and/or temperature probes for the same which will at least go some way toward overcoming the above disadvantages or which will at least provide the public with a useful choice.

Accordingly, in one aspect the invention consists in a combination of a heater connection means and a temperature sensor for apparatus for humidifying gases. The apparatus comprises a liquid compartment, a liquid supply inlet through which liquid is in use supplied to the liquid compartment, a gases passageway through which gases are supplied to pass over a microporous wall common to both the liquid compartment and the gases compartment to a point of use. The microporous wall is permeable to vapour but substantially impermeable to liquid. Heating means are provided, energisable to heat the liquid to generate vapour pressure within the liquid compartment sufficient to cause passage of vapour but not liquid through the microporous wall, the heating means having energy supply connection means. The combination has a first temperature sensor for sensing the temperature of gases in the gases passageway and the heater connection means are provided for interconnection with the energy supply connection means for supplying energy to the heating means. The construction and arrangement is such that only when the first temperature sensor is disposed within the gases passageway are the energy supply connection means interconnected with the heater connection means and energy supplied to the heating means.

In a further aspect the invention consists in a combination of a heater connection means and a temperature sensor for apparatus for humidifying gases, the apparatus comprises a liquid supply means, liquid heating means energisable to heat liquid in the liquid supply means, a gases passageway through which gases pass from a gases supply means to a point of use, and vapour transfer means whereby vapour but not liquid is transferred from the liquid supply means to the gases passageway. The heating means or the apparatus has energy supply connection means, and the combination has a first said temperature sensor for sensing the temperature of gases in the gases passageway and has heater connection means for interconnection with the energy supply connection means for supplying energy to the heating means The construction and arrangement is such that only when the first temperature sensor is disposed within the gases passageway is the energy supply connection means interconnected with the heater connection means and energy supplied to the heating means.

In a still further aspect the invention consists in apparatus for humidifying gases. The apparatus comprises a liquid supply means, liquid heating means energisable to heat liquid in the liquid supply means, a gases passageway through which gases pass from a gases supply means to a point of use, and vapour transfer means whereby vapour but not liquid is transferred from the liquid supply means to said gases passageway. A temperature probe is also provided having a temperature sensor, the probe is adapted to be removably associated with the gases passageway in a manner such that the temperature sensor is positioned to sense the temperature of gases flowing in the gases passageway. The heating means or the apparatus has energy supply connector means for interconnection with heater connector means provided on a temperature probe for use with the apparatus. The construction and arrangement is such that only when the first temperature sensor is disposed within the gases passageway is the energy supply connection means interconnected with the heater connection means and energy supplied to the heating means.

In a still further aspect the invention consists in apparatus for humidifying gases. The apparatus comprises a liquid compartment, a liquid supply inlet through which liquid is in use supplied to the liquid compartment, a gases passageway through which gases are supplied to pass over a microporous wall common to both the liquid compartment and the gases passageway at a point of use. The microporous wall is permeable to vapour but substantially impermeable to liquid. Heating means are provided, energisable to heat the liquid to generate vapour pressure within the liquid compartment sufficient to cause passage of vapour but not liquid through the microporous wall. A temperature probe is also provided, having a temperature sensor. The probe is adapted to be removably associated with the gases passageway in a manner such that the temperature sensor is positioned to sense the temperature of gases flowing in the gases passageway. The heating means or the apparatus have energy supply connector means for interconnection with heater connector means provided on the temperature probe for use with said apparatus. The construction and arrangement is such that only when the first temperature sensor is disposed within the gases passageway is the energy supply connection means interconnected with the heater connection means and energy supplied to the heating means.

In a still further aspect the invention consists in a gases distribution passageway for providing a tortuous path for gases passing therethrough. The passageway comprises a gases body defining outer walls thereof, and a part of the walls define an inlet conduit for gases to enter the passageway and a first outlet for gases to exit the passageway. The passageway has support means therein for supporting a liquid body within the passageway with gases paths enabling gases to pass over and around the liquid body. The inlet and the first outlet conduit are provided on opposite sides of the liquid body and substantially perpendicular to said liquid body such that gases enter the passageway through the inlet in a direction substantially perpendicular to the liquid body and pass in divided form over and around the liquid body before exiting from the passageway through the first outlet conduit in a direction substantially perpendicular to the liquid body.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the invention will now be described with reference to the accompanying drawings in which.

DETAILED DESCRIPTION OF THE PREFERRED EMBODIMENTS

Figure 1:
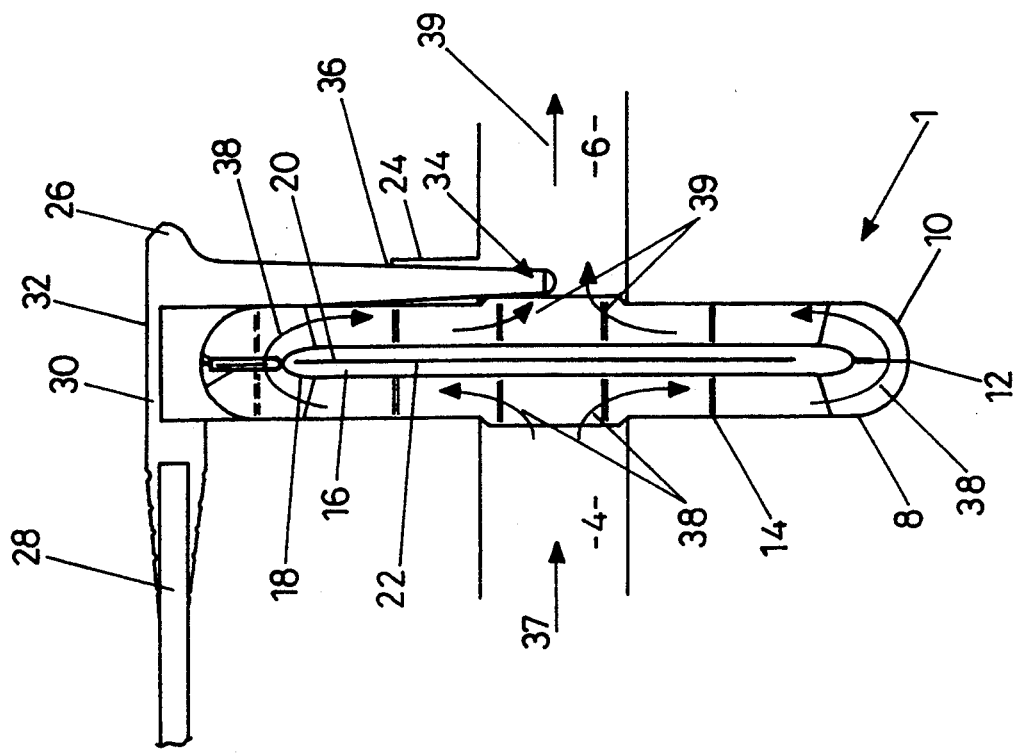
FIG. 1 is a front elevation in cross section of a humidifier apparatus and temperature probe and heater connection in accordance with the present invention.

Referring to the drawings, a humidifier apparatus according to the invention is shown in FIG. 1 generally referenced 1. The apparatus has a generally hollow body 2 the walls of which define a gases passageway comprising a gases distribution chamber preferably made of a plastics material and having a gases inlet 4 and a gases outlet 6. The gases inlet and gases outlet are designed to be connected to tubular gas conduits between a supply of such gases and a patient for example a hospitalised patient in need of humidified gases. The body 2 is preferably constructed from two hollow casings 8 and 10 which are joined about a mid-point shown by line 12. A gas tight seal is made between the hollow casings by use of for example an adhesive or a plastic solvent or a compressible gasket or welding.

Figure 6:
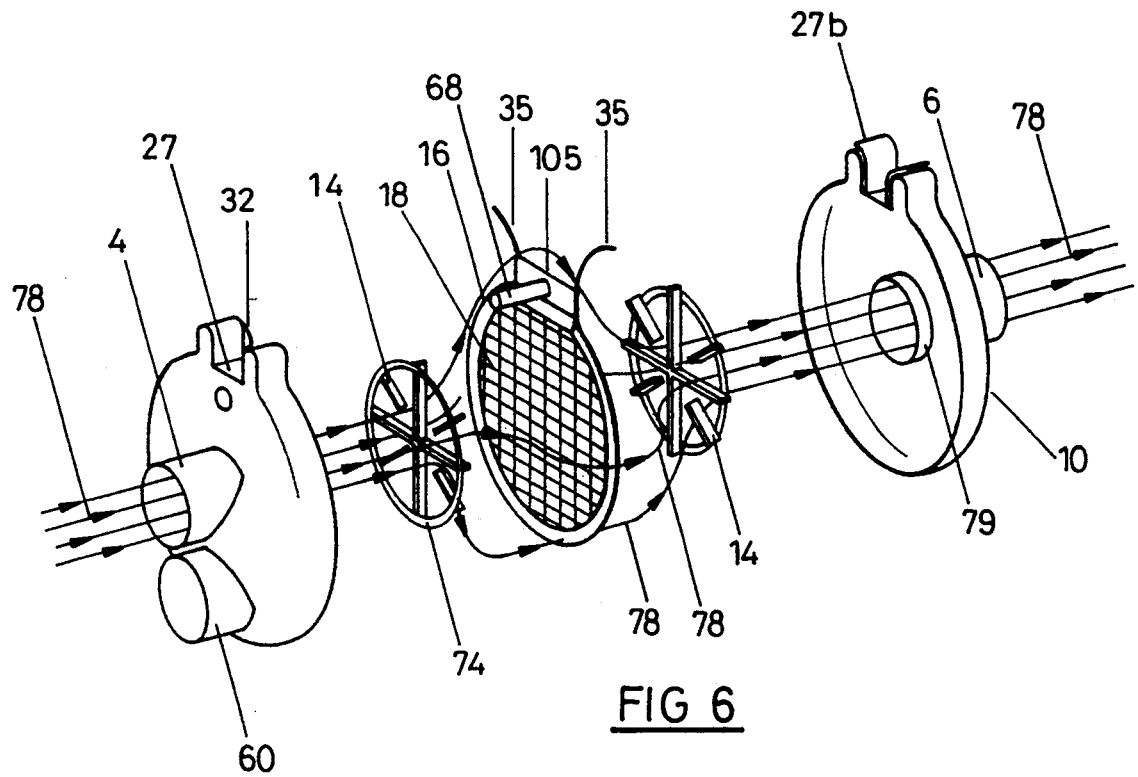
FIGS. 6 and 7 are exploded view of the humidifier apparatus of FIG. 5 showing gases flow through the apparatus.
Figure 7:
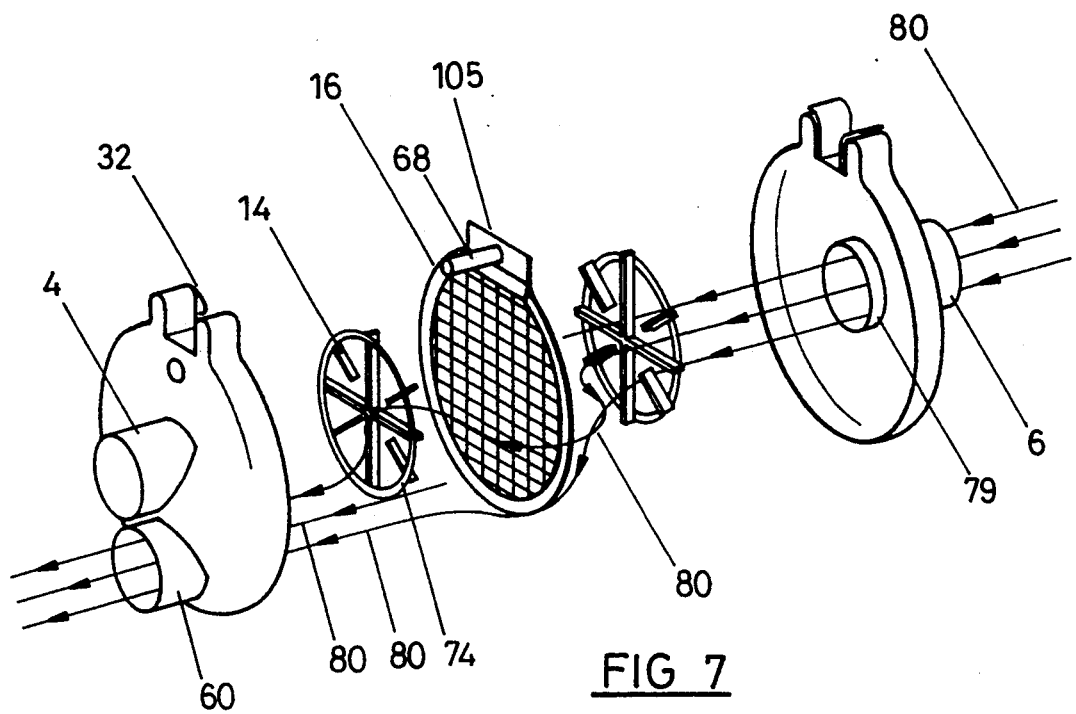
Figure 9:
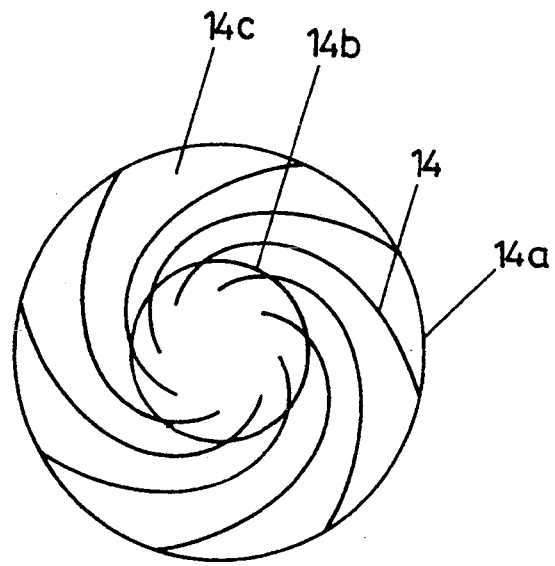
FIG. 9 is an end elevation of a gases distribution means in accordance with the present invention.

The body 2 contains support means 14c (FIG. 9) comprising ribs 14 which locate and support a preferably substantially planar body such as liquid compartment 16 relative to the body 2 in a position such that gases may flow over and around the body while passing from the inlet 5 to the outlet 6. The ribs 14 of the support means 14c are provided in the form of vanes attached to locating rings 14a and 14b and may be moulded as part thereof. The ribs or vanes 14c may be either radially oriented as shown in FIGS. 6 and 7 or spirally oriented as shown in FIG. 9 dependent on the air flow required through the apparatus. Thus support means also provide flow directing means to direct gases flow over the outer surface of the liquid compartment 16 as will be described further below.

In the preferred form of the invention vapour transfer means to transfer vapour but not liquid to the gases flow in the passageway comprise the liquid compartment 16 which is constructed from microporous sheet material 18 having sealed edges 20 as described in our U.S. Pat. No. 5,062,145, the specification of which is incorporated herein by reference other known transfer means may be provided. The microporous material 18 is substantially permeable to vapour such as water vapour but substantially impermeable to liquid such as liquid water and is made from, for example, expanded PTFE (polytetrafluoroethylene). Such sheet material is manufactured under the trade mark GORTEX and is available from W. L. Gore & Associates Inc. Delaware, USA, in various thicknesses and dimensions. To form the microporous envelope comprising liquid compartment 16, the sheet material 18 is cut into an appropriate shape for example two circular shapes and the edges of the two circles are fixed to each other for example by injecting a plastics material for example polypropylene about the contacting edges to produce a sealed edge 20. Alternatively, another shape for example a rectangular shape could be used whereby the material is folded and the edges again fixed to each other by injecting a plastics material about the contacting edges. The plastics material of the sealed edges 20 also provides mounting means for helping to locate the water compartment 16 between support means comprising supporting members 14. A water entry tube to allow liquid such as water to enter the liquid compartment 16 is provided and the water tube is connected to a supply of water. The liquid compartment contains a heating means comprising electrical heating element 22 which is located within the liquid compartment. In the preferred form of the invention the heating element 22 is provided as a flat spirally wound element in the form of disc wound preferably as a single layer flat coil from an enamelled copper wire preferably with turns epoxied or otherwise bonded to each other. The reason for providing the flat spiral arrangement is that in some circumstances air, gas or water vapor can be occluded within the water compartment 16 and if parts of the heating element are in an air bubble formed by that occluded air then the heating element could heat up and damage that area of the heating element and leading to failure of the heating element. We have found that if a plurality of turns of wire in single layer flat coil form are partially exposed to air, then because of conductivity from the portions of turns in air to portions of turns in water, and to adjacent turns, if epoxied together, a lesser damaging effect is given compared with a whole turn of, for example, a tubular wound coil from heating element in which full turns are exposed to air and therefore run the risk of overheating. Alternatively, the heating element may comprise a printed circuit or etched foil format on a rigid or preferably flexible substrate (e.g. Kanthal or Minco types); or alternatively a semi-conductive material (as for example used in PTC heaters made by Hartford Eichenauer or TDK Corporation) or a composite of insulating conductive materials such as carbon filled plastics or carbon filled synthetic rubbers (for example Premix OY, or Jamak INC respectively). These latter materials maybe made into a suitable shape (such as a rectangle) with suitably connected metal electrodes (for example inserted or crimped down to opposite edges) to form a non-wound heater with suitable positive temperature co-efficient of resistance to facilitate temperature measurement by resistance measurement and have some degree of temperature self limiting due to resistance increase at elevated temperatures.

The heating element 22 may be encapsulated by or bonded to a heat sink (not shown) comprising a quantity of thermally conductive heat sink material, preferably metal (for example brass) positioned within the liquid compartment 16. In the preferred form this is circular or rectangular in shape and is thermally bonded to the heating element 22 with heat bonding epoxy. The purpose of the heat sink is to spread the heat generated by the heating element evenly, further preventing hot spots.

The heat sink may also provide a site for overheat sensing.

In order to disperse water across the element/heat sink interface under all conditions a sheath or layer(s) of absorbent material may be located within the water compartment 16 adjacent to the heat sink or the element. The sheath or layers of absorbent material (not shown) are preferably made of cotton based paper having superior wicking properties. Such paper may be punched with holes to control the relative paper area.

Figure 14:
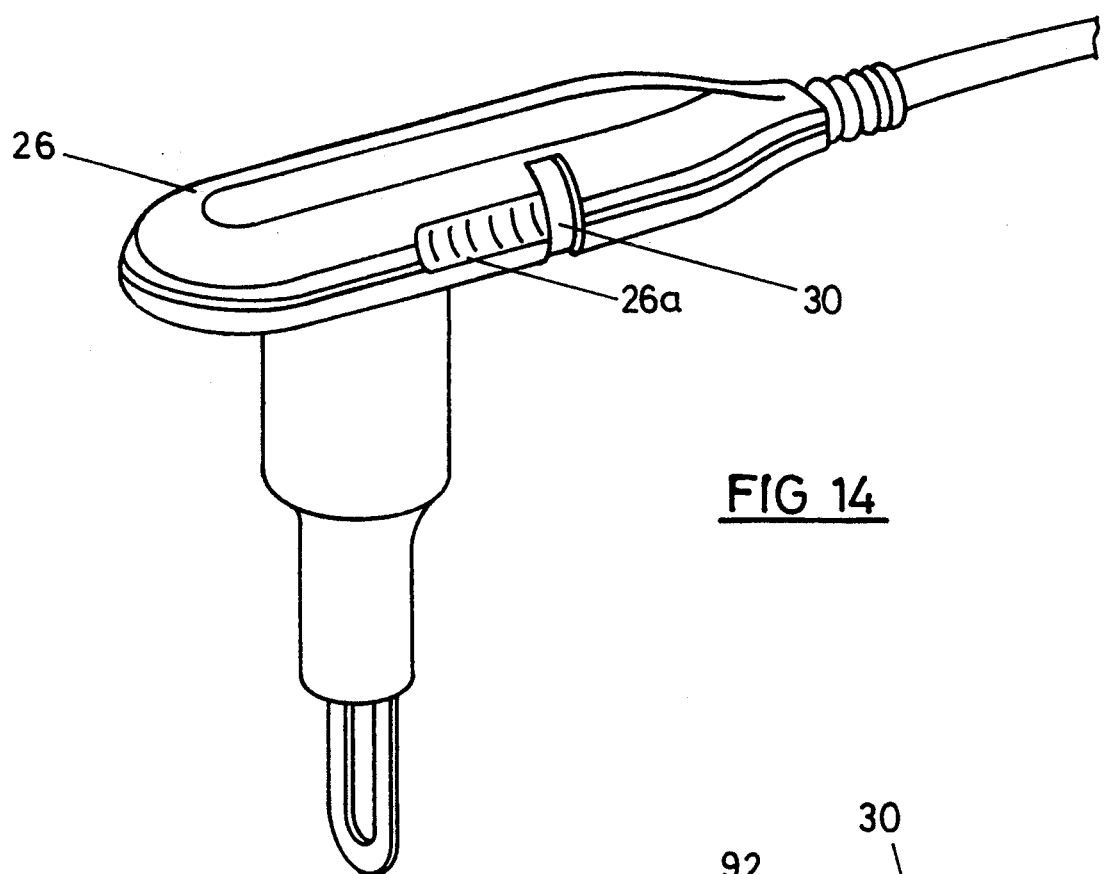
FIG. 14 is a perspective view of a temperature probe in accordance with the present invention.
Figure 15:
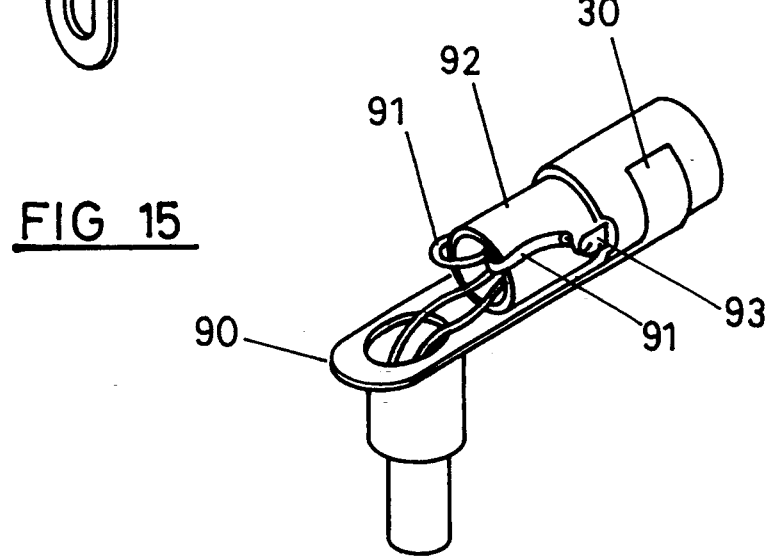
FIG. 15 is a perspective view of a partially assembled temperature probe in accordance with the temperature probe of FIG. 14.

Referring to FIG. 1, the gases outlet 6 and/or the portion of the walls of the body 2 adjacent to the outlet 6 or inlet 4 has a sensor support member aperture 24 therein for accommodating part of a combined temperature probe and heater supply connector forming a combination reference 26. The combination 26 has a cable 28 which provides electrical energy to a heater connector means comprising contacts 30 on the probe and provides a connector to a temperature sensor 34 also provided on the probe and mounted in use in the gases flow path. The body 2 of the apparatus has energy supply connector means comprising sprung contacts 32 connected to for connection with contacts 30 on the probe in order to supply electrical energy to the heater. Alternatively, the heater may have contacts which protrude through body 2 to engage directly with contacts 30 (FIG. 14) on the probe. Referring to FIG. 15 the combination 26 is shown in a partially assembled form about a probe core 90. The remaining outer portions of the combination 26 are over moulded onto the probe core 90. Contacts 30 have lugs 93 thereon for soldering heater connector wires 91 which are disposed within probe cable outer 92.

Figure 13:
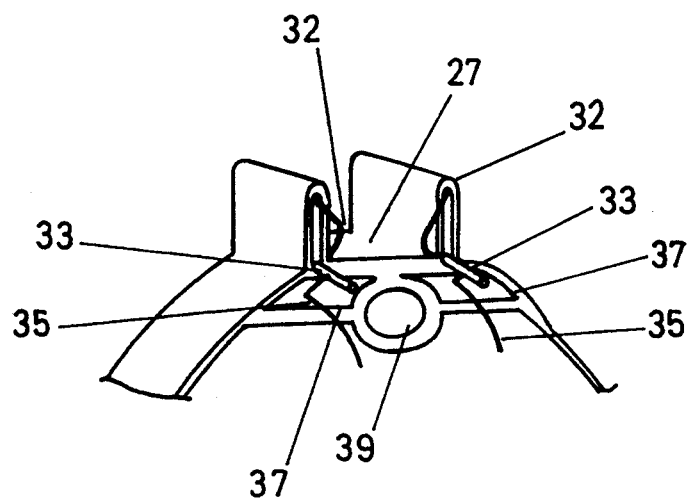
FIG. 13 is a perspective view of an upper part of one half of the humidifying apparatus of the preceding figures.

In order to accommodate the combination 26, the body 1 of the humidifier apparatus has raised portions which form a guide 27 in the form of a gap (FIG. 4) the shape of which corresponds to the contour of part of the body of the combination 26. The sprung contacts 32 are provided either side of the guide 27 as shown in more detail in FIGS. 13 and 16. The shape of the contacts may enable a mechanical connection to be made between the sensor and the humidifier apparatus when the sensor is pressed downwardly into place in the guide 27. Preferably, however, a mechanical connection between the body 2 and the combination 26 is made by resilient member 27b (FIG. 5). Member 27b is fixedly located in guide 27 and has contoured sides which may be flexibly forced away from each other slightly so as to accommodate combination 26 therebetween. The sides of member 27b are contoured to engage with depressions 26a (FIG. 14) of the sides of combination 26 and so make a mechanical connection between the body 2 and combination 26. The contacts 32 have projecting portions 33 which extend or project from one half of the humidifier body as will be explained further later with reference to FIG 13. The portions 33 are provided so that wire ends 35 of the heater 22 may be wound onto contacts 33 and preferably soldered thereto as shown in FIG. 13. Also, spaces 37 are left in the body so that a loop of heater wire may be provided therein to prevent undue stress being placed on the wire. A hole 39 is also provided so that a water tube to the liquid chamber may enter the apparatus as will be described further below. In use, the probe 26 must be firmly located so that contacts 32 and 30 make electrical contact and in order for this to occur, the probe must be firmly in position so that the temperature sensor 34 will preferably be located within or adjacent to outlet 6 of the gases compartment, the surfaces about aperture 24 making a substantially gas tight seal with the corresponding surfaces 36 of the combination 26. In this way, the heater 22 cannot be energised unless the control means (not shown) are provided with an indication of the gases temperature of the humidified gases which have passed over the liquid compartment 16. This is advantageous, since if no temperature measurements were supplied to the control means then the control means could continue to supply energy to the heater which could result in a dangerously high gases temperature being supplied to the patient. Also, such high temperatures could damage the apparatus.

Referring to FIG. 1, in use, the gases enter the apparatus through inlet 4 in a direction substantially perpendicular to the substantially planar surfaces of the liquid compartment 16 as shown by arrow 37. The gases then encounter the microporous wall 18 of the liquid compartment and are directed over the surfaces of the liquid compartment by the ribs or fins 14 of the flow directing means 14c as shown by arrows 38. The gases then flow around the edges of the compartment 16 and over the other side of the microporous wall and exit the apparatus through outlet 6 in a direction which is substantially perpendicular to the microporous wall of liquid compartment 16 and which is parallel to the direction of entry of gases into the apparatus.

Figure 2:
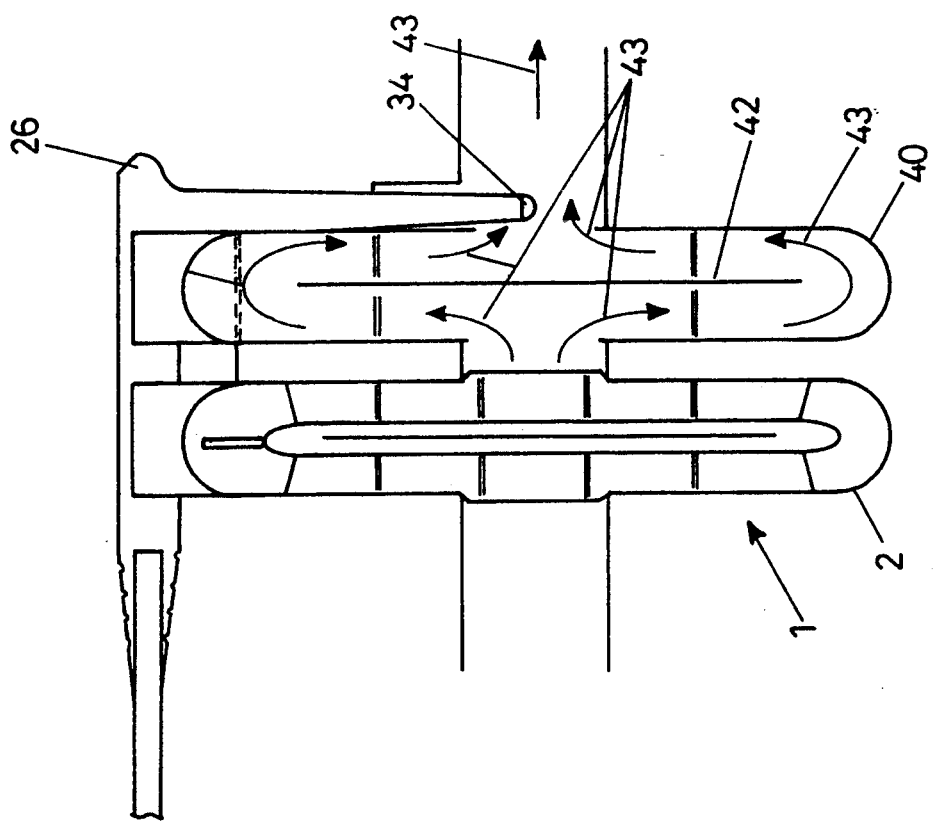
FIG. 2 is an elevation in cross section of a humidifier apparatus, a gases distribution chamber, and a temperature probe in accordance with the present invention.

Referring to FIG. 2, the humidifier apparatus 1 as described with reference to FIG. 1 above is shown with an additional gases distribution chamber 40 in gaseous connection therewith. The distribution chamber 40 is substantially the same as that described with reference to FIG. 1 above, however, the water compartment 16 is not provided between the support members 14c. Instead, a baffle 42 is provided and a tortuous path for the gases which have passed over liquid compartment 16 of the humidifying apparatus 1 is provided around the baffle 42. The tortuous path provided by baffle 42 ensures that the gases which have passed over water compartment 16 and including vapour from that compartment of the humidifier apparatus have mixed thoroughly in order to provide a humidified gas and the temperature of this humidified gas is sensed by temperature sensor 34 of the combination 26. The direction of flow of gases about baffle 42 is indicated by arrows 43.

Figure 4:
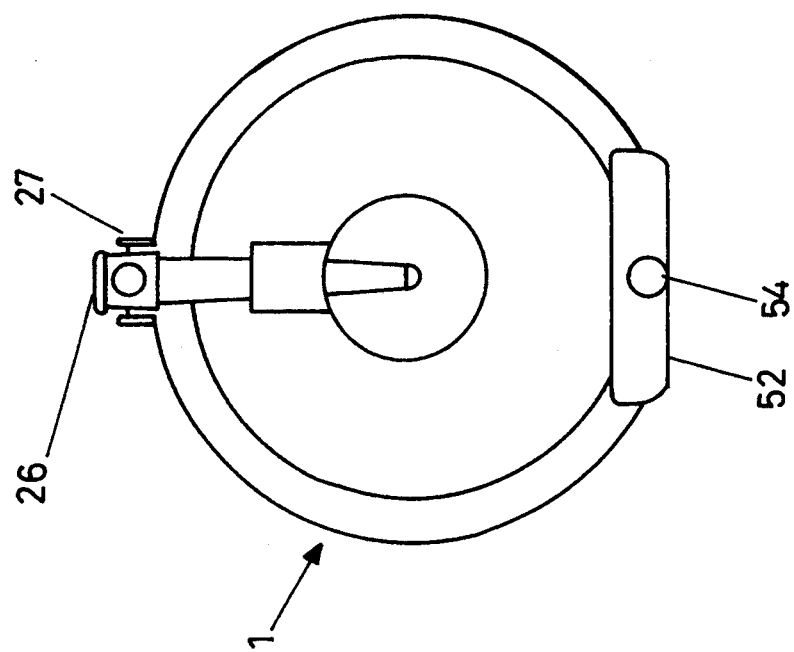
FIG. 4 is an end elevation of the humidifier apparatus and temperature probe of FIG. 3.
Figure 3:
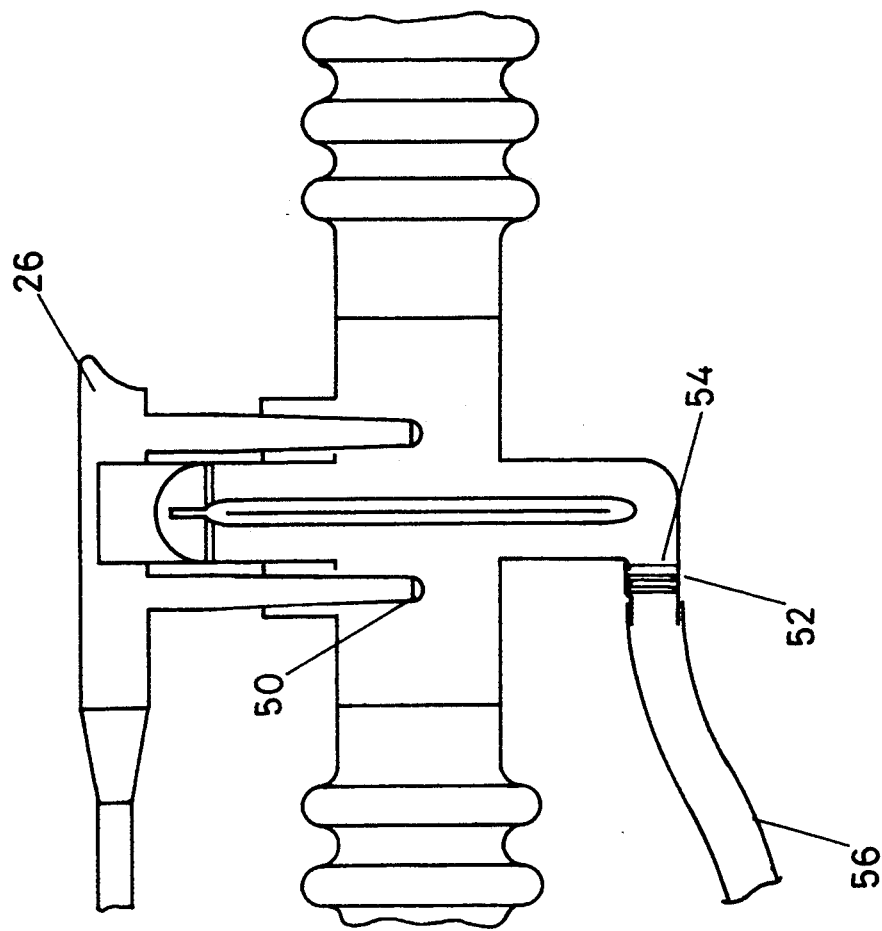
FIG. 3 is an elevation in cross section of a humidifier apparatus including condensation removal means and another form of temperature probe in accordance with the present invention.
Figure 5:
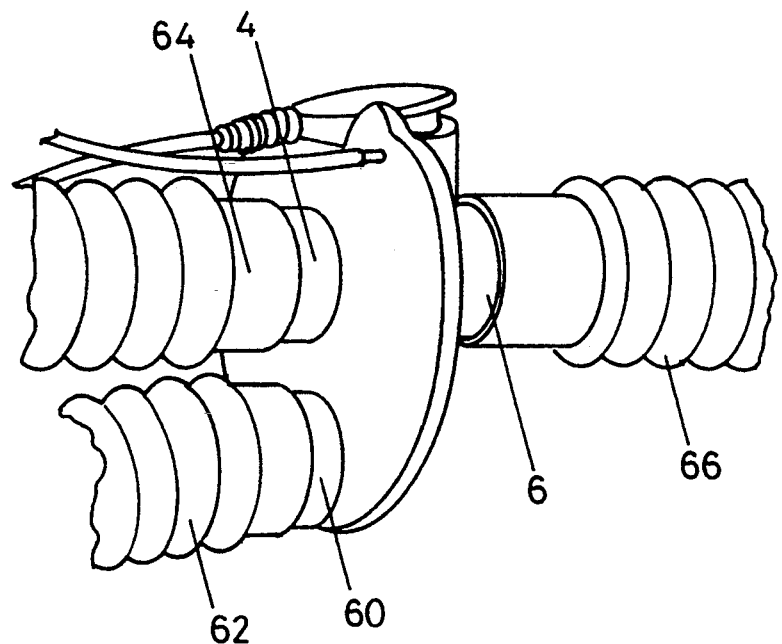
FIG. 5 is a perspective view of a further form of humidifier apparatus in accordance with the present invention.

Referring to FIGS. 3 and 4, humidifier apparatus as described with reference to FIG. 1 above is shown. However, in FIG. 3, an additional temperature sensor 50 is provided mounted on the combination 26 and removable therewith. The additional temperature sensor 50 is located in a further aperture 24 on the side of the humidifier apparatus which receives gases from a gas supply which is to be humidified. The temperature sensor comprises for example a thermistor or other temperature measuring or indicating device. The second temperature sensor 50 may be used to detect stationary or backwards flow of gases through the gases compartment by measuring the relative rise in temperature at entry 4 and corresponding drop in temperature at the outlet 6 sensed by temperature sensor 34. This additional feature enables the heating and humidification of the gases to be synchronised with breathing of the patient, as well as terminating humidification when the gas flow is stopped or disconnected.

The positioning of temperature sensor 34 to the heater element has the advantage that should there be overheating of the gases for any reason, the probe will transmit a suitable signal to control apparatus (not shown) which will cause appropriate operation of either the heating element or the flow of gases or otherwise to control the flow of gases, water, or heat so as to assist in ensuring the safe supply of humidified heated gases to a destination such as a hospitalised patient.

Inlet 4 is usually connected to a "Y" connector comprising a gases tube or conduit having a bifurcation therein. One branch from the bifurcation is connected to the inspiratory conduit of a breathing circuit and the other branch is connected to the expiratory conduit of the breathing circuit so that gases being supplied to and from the patient pass through the humidifier apparatus in alternate directions as the patient inhales and exhales. By connecting the humidifier apparatus using a "Y" connector in close proximity to a patient in what is medically known as the "dead space", only a small volume of the gases in the breathing circuit needs to be humidified by the apparatus.

The control of heat and water supplied to the water compartment 16 is substantially in accordance with our U.S. Pat. No. 4,708,831, the specification of which is incorporated herein by reference.

In FIG. 3 a condensation removal means comprising orifice 52 is shown. Orifice 52 is provided at a location in body 1 of the humidifier apparatus which corresponds to an area adjacent to the water compartment 16 where condensation is likely to collect due to gravitational effects for example. The orifice 52 is provided with a substance in the form of a plug or membrane 54 for example of material which is substantially water permeable and substantially gas impermeable for material absorbent material preferably cotton based paper. Thus the material 54 allows condensation to pass out of the humidifying apparatus and into a condensation removal conduit 56. The material 54 is sufficiently gas impermeable to prevent any substantial leakage of gases therethrough so that the control means does not detect any reduction in gas pressure. Thus material 54 substantially prevents humidified gases within the humidifier apparatus from entering the condensation removal conduit 56.

A further form of humidifying apparatus as shown in FIG. 5. Referring to FIG. 5 a humidifier apparatus substantially the same as those previously described is shown and the references for the humidifying apparatus shown in FIG. 5 are consistent with the features of the humidifiers previously described. The humidifier apparatus of FIG. 5, however, has a second outlet 60 which is positioned in a lowermost part of the distribution chamber where condensation from the humidified gases within the chamber tends to collect in use. The second outlet 60 is in use connected to an expiratory tube or conduit 62 and the inlet 4 is in use connected to an inspiratory tube or conduit 64 through which a patient breathing through a face mask for example connected to tube or conduit 66 which is connected to a first outlet 6 would usually inhale gases from a source of gases such as a ventilator machine. Thus with the arrangement shown in FIG. 5, a "Y" connector is not necessary.

Figure 16:
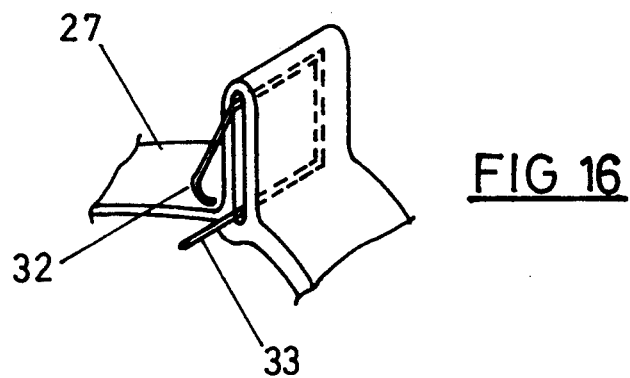
FIG. 16 is a perspective view showing more detail of a part of the apparatus shown in FIG. 13.

Referring to FIG. 6 and FIG. 16 the humidifier apparatus of FIG. 5 is shown in a disassembled form. The water compartment 16 is shown in more detail together with a water supply opening 68 for connection to a supply of water for the water compartment. The energy supply connector means comprising sprung contacts 32 is also. The support means 14 are also shown in more detail, the support means being arranged in radial segments supported by an annular ring 74, or preferably as form shown in FIG. 9, the radial or preferably spiral arrangement of the fins 14 of the support means also providing gases distribution means to distribute the gases over the microporous wall 18 of the water compartment. In FIG. 6, the arrows 78 show the direction of gases flow through the distribution chamber from the inlet 4 to the outlet 6 when a patient is inhaling for example.

The lip 79 in FIGS. 6 and 7 helps prevent accidental flow of any liquid such as condensate in the chamber into the outlet 6. Thus if the apparatus is accidentally tipped on an angle so that outlet 6 is in a lower position then lip 79 will tend to act as a barrier to prevent liquid in the chamber from entering the outlet 6 and the outlet conduit.

Referring to FIG .7 the apparatus of FIGS. 5 and 6 is shown. In FIG. 7 arrows 80 show the flow of gases through the distribution chamber from the outlet 6 to the second outlet 60. The positioning of the second outlet 60 in a lowermost portion of the chamber tends to minimise any flow of exhaled gases (shown by arrows 80) over the upper portion of the water compartment 16. The positioning of the second outlet 60 in a lowermost position also provides an outlet for removal of condensation which builds up in the distribution chamber, so that this condensation tends to collect due to gravity in the lowermost portion and such condensate travels out of the distribution chamber through second outlet 60 and is removed by a condensation removal device located in the expiratory tube or conduit 62. The inlet 4 and the second outlet 60 may also be directed away from the chamber at angles so that the conduit 64 and 62 tend to spread away from each other and thus the distribution chamber will tend to lie in a stable position across the chest of a patient for example and be orientated such that the combination temperature probe heater supply connector 26 is in an uppermost position and the second outlet 60 is in a lowermost position.

In the part of the distribution chamber which includes the inlet 4 and second outlet 60 has a channel connecting these two openings to the chamber provided in the outer surface of the chamber. This assists in allowing gases to pass between these openings during Constant Positive Airway Pressure (CPAP) usage of the apparatus. This is desirable since without the channel gases tend to enter the chamber during this mode of operation and cool at least one side of the microporous envelope.

Figure 8:
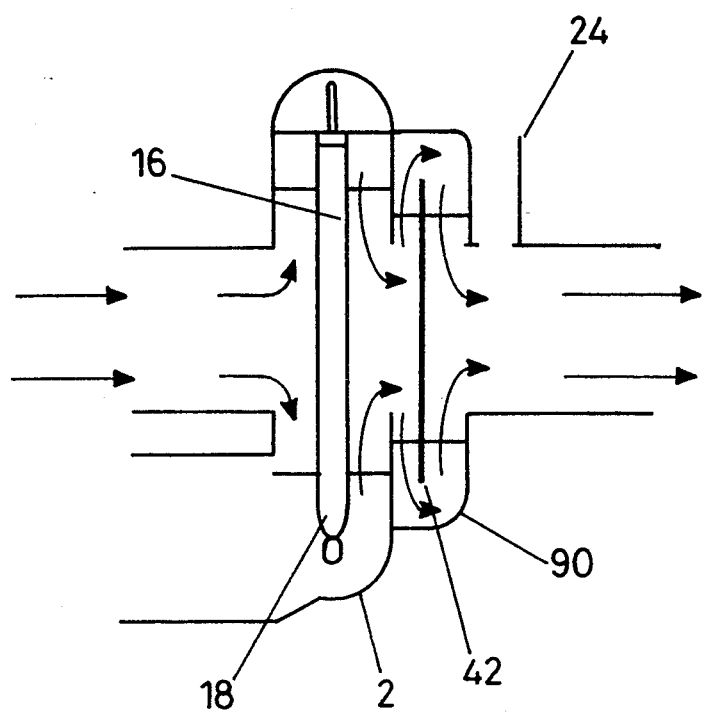
FIG. 8 is an elevation in cross section of a further humidifier apparatus in accordance with the present invention.

A further form of humidifier apparatus is shown in FIG. 8, being an improved version of the device shown in FIG. 2. Referring to FIG. 8, a humidifier apparatus similar to that described with reference to FIGS. 5, 6 and 7 is shown. However, the main gases distribution chamber 2 has a further gases distribution chamber 90 attached thereto. The further gases distribution chamber 90 may be moulded as an integral part of the apparatus or may be attached to the distribution chamber 2 by use for example of an adhesive or a plastic solvent or a compressible gasket or by ultrasonic welding. The apparatus has a sensor support member aperture 24 as previously described with reference to FIGS. 1 and 2 for accommodating a sensor support member having a temperature probe thereon. The further gases distribution chamber 90 has a baffle means comprising a baffle member 42 therein for providing a longer air path for gases passing through the apparatus for improved control of temperature as described with reference to FIG. 2 above.

Referring to FIG. 9, a further form of the support means 14 referred to above is shown. In FIG. 9, the supporting ribs 14 are arranged in a spiral form to form a spiral support plate. The fins in such a spiral form provide improved flow of air from cooler to warmer surface areas of the microporous walls 18 of the water compartment 16.

Figure 10:
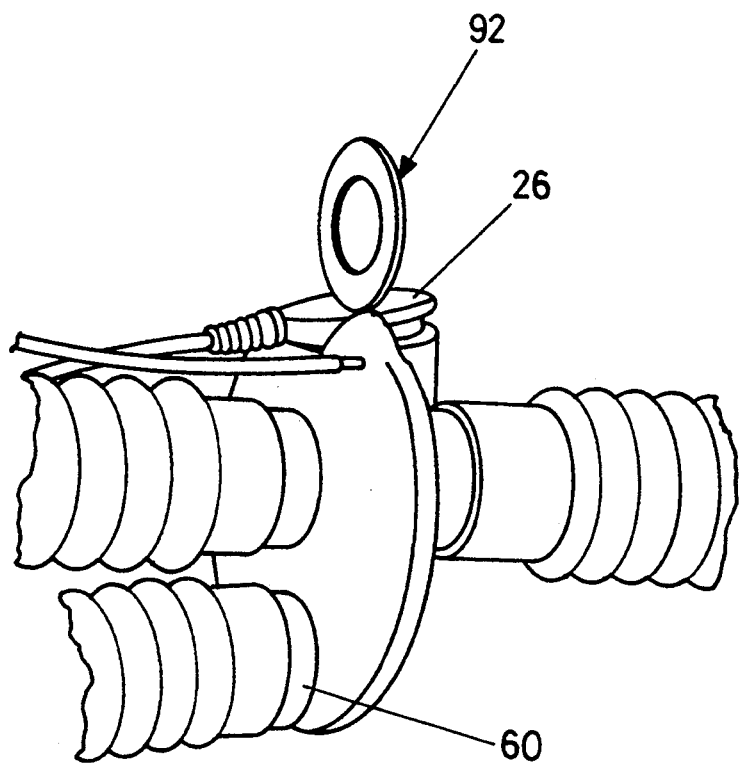
FIG. 10 is a perspective view of a further humidifier apparatus in accordance with the present invention.

FIG. 10 is a perspective view of humidifier apparatus substantially as previously described but further including a ring 92 for attaching the humidifier apparatus to a support device. In use, the user places ring 92 over a projection such as a hook of a supporting device so that the humidifier apparatus is suspended from the device. The position of ring 92 adjacent to the position at which the temperature probe 26 would normally be placed in use, ensures that the device is suspended in a position such that any condensate collecting within the device would normally drain toward expiratory tube outlet 60 of the device.

Figure 11:
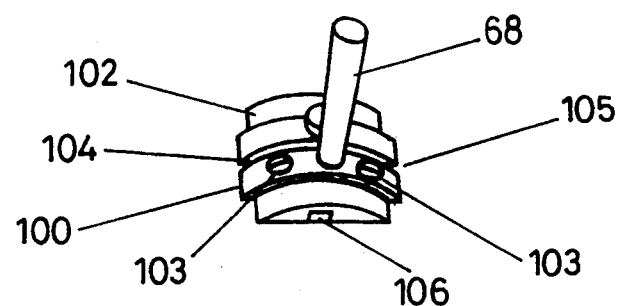
FIG. 11 is a perspective view of a part of a liquid supply member.
Figure 12:
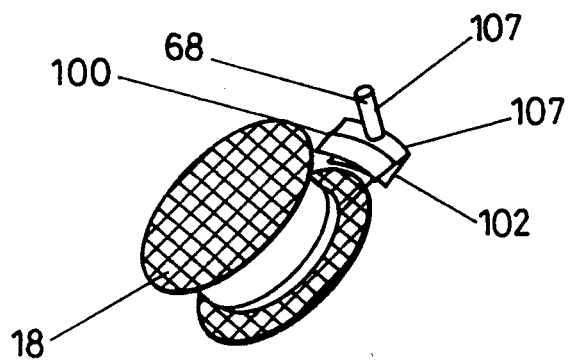
FIG. 12 is an exploded perspective view of a liquid compartment in accordance with the present invention.

Referring to FIG. 11 the water supply tube attachment 105 for the microporous water containing envelope is shown. The device is located in an upper portion of the microporous envelope and generally comprises the water tube attachment or water supply opening 68 (which enters or exits the apparatus through aperture 39 shown in FIG. 13) which is placed on one of two side portions 100 and 102. The device of FIG. 11 is preferably moulded from a plastics material, and the area 104 between portions 100 and 102 is sufficiently flexible to allow the two portions to be bent as shown in FIG. 12. A small channel 106 is provided on the undersurface of the portion having the member 68. The channel leads from the edge of that portion to the member 68 so that when the device is bent as shown in FIG. 12, the channel overcomes the problem of producing a perpendicularly oriented water supply tube by providing access of a liquid between the folded portions 100 and 102 to the member 68. In use the microporous envelope is assembled by placing the heater coil in the paper/cotton sheath and placing the microporous material either side of the sheath. The portions 100 and 102 of the device of FIG .11 is then folded about an edge of the assembled materials and the heater wires 35 are also disposed between the portions 100 and 102. The assembly is then placed in a mould and a plastics material such as that marketed under the trade mark SANTOPRENE is moulded about the edges of the assembly to seal it as shown in FIGS. 6 and 7. Holes 103 are also provided (FIG. 11 to allow the moulded material to surround the wires 35 and make a sealing contact with them.

From the foregoing it will be seen that humidifier apparatus is provided which will accept a combination temperature probe and heater supply connector and the heating means within the humidifier apparatus will not be activated unless the probe is in the correct position so that temperature sensors in the probe can pass indications of gases temperature to control apparatus. In other words it will be seen that the supply of energy to the heater cannot be effected unless the temperature sensor(s) is or are appropriately positioned in the gases passageway. Also, a humidifier is provided which has a condensation removal means to minimise any undesirable build up of condensation within the humidifier apparatus.

Furthermore, the device is very compact having a gases space volume of for example 60 mls and being very short so that the reduced and the device may be located within the "dead space" and thus reduce the volume of humidified gases in the breathing circuit to a minimum.

We claim:

1. A combination of a heater connection means and a temperature sensor for apparatus for humidifying gases, said apparatus comprising a liquid compartment, a liquid supply inlet through which liquid is in use supplied to said liquid compartment, a gases passageway through which gases are supplied to pass over a microporous wall common to both said liquid compartment and said gases compartment to a point of use, said microporous wall being permeable to vapour but substantially impermeable to liquid, heating means energisable to heat said liquid to generate vapour pressure within said liquid compartment sufficient to cause passage of vapour but not liquid through said microporous wall, said heating means having energy supply connection means, said combination having a first said temperature sensor for sensing the temperature of gases in said gases passageway and having heater connection means for interconnection with said energy supply connection means for supplying energy to said heating means, the construction and arrangement being such that only when said first temperature sensor is disposed within said gases passageway is said energy supply connection means interconnected with said heater connection means and energy supplied to said heating means.

2. A combination as claimed in claim 1 wherein said first temperature sensor is positioned to sense the temperature of gases which have passed over said microporous wall.

3. A combination as claimed in claim 1 or claim 2 wherein said first temperature sensor is provided on a sensor support member of said combination.

4. A combination as claimed in claim 3 wherein a wall defining a sensor support member aperture is provided in said gases passageway for accommodating said sensor support member.

5. A combination as claimed in claim 4 wherein a surface of said wall is configured to make a sealing contact with a surface of said sensor support member so as to substantially prevent gases in said gases passageway from escaping therefrom.

6. A combination as claimed in claim 1 wherein said combination has a second temperature sensor for sensing the temperature of gases in said gases passageway, said second sensor sensing the temperature of gases in said gases passageway before said gases pass over said microporous wall when said energy supply connection means are interconnected with said heater connection means.

7. A combination as claimed in claim 1 wherein baffle means are provided between said microporous wall and said first temperature sensor to provide a tortuous path for humidified gases therebetween.

8. A combination of a heater connection means and a temperature sensor for apparatus for humidifying gases, said apparatus comprising a liquid supply means, liquid heating means energisable to heat liquid in said liquid supply means, a gases passageway through which gases pass from a gases supply means to a point of use, vapour transfer means whereby vapour but not liquid is transferred from said liquid supply means to said gases passageway, said heating means or said apparatus having energy supply connection means, said combination having a first said temperature sensor for sensing the temperature of gases in said gases passageway and having said heater connection means for interconnection with said energy supply connection means for supplying energy to said heating means, the construction and arrangement being such that only when said first temperature sensor is disposed within said gases passageway is said energy supply connection means interconnected with said heater connection means and energy supplied to said heating means.

9. A combination as claimed in claim 8 wherein said vapour transfer means comprises a liquid compartment to which liquid is supplied by said liquid supply means, said liquid compartment having a microporous wall common to both said gases passageway and said liquid compartment.

10. A combination as claimed in claim 9 wherein said first temperature sensor is positioned to sense the temperature of gases which has passed over said microporous wall.

11. A combination as claimed in claim 8 wherein said first temperature sensor is provided on a sensor support member of said combination.

12. A combination as claimed in claim 11 wherein a wall defining a sensor support member aperture is provided in said gases passageway for accommodating said sensor support member.

13. A combination as claimed in claim 12 wherein a surface of said wall is configured to make a sealing contact with a surface of said sensor support member so as to substantially prevent gases in said gases passageway from escaping therefrom.

14. A combination as claimed in claim 9 wherein said combination has a second temperature sensor for sensing the temperature of gases in said gases passageway, said second sensor sensing the temperature of gases in said gases passageway before said gases pass over said microporous wall when said energy supply connection means are interconnected with said heater connection means.

15. A combination as claimed in claim 9 wherein baffle means are provided between said microporous wall and said first temperature sensor to provide a tortuous path for humidified gases therebetween.

16. Apparatus for humidifying gases, said apparatus comprising a liquid supply means, liquid heating means energisable to heat liquid in said liquid supply means, a gases passageway through which gases pass from a gases supply means to a point of use, vapour transfer means whereby vapour but not liquid is transferred from said liquid supply means to said gases passageway, a temperature probe having a temperature sensor said probe being adapted to be removably associated with said gases passageway in a manner such that said gases sensor is positioned to sense the temperature of gases flowing in said gases passageway, said heating means or said apparatus having energy supply connector means for interconnection with heater connector means provided on a temperature probe for use with said apparatus, the construction and arrangement being such that only when said first temperature sensor is disposed within said gases passageway is said energy supply connection means interconnected with said heater connection means and energy supplied to said heating means.

17. Apparatus as claimed in claim 16 wherein said vapour transfer means comprises a liquid compartment to which liquid is supplied by said liquid supply means, said liquid compartment having a microporous wall common to both said gases passageway and said liquid compartment.

18. Apparatus as claimed in claim 16 or claim 17 wherein a wall defining a sensor support member aperture is provided in said gases compartment for accommodating said sensor support member.

19. Apparatus as claimed in any one of claim 18 wherein a surface of said wall is configured to make a sealing contact with a surface of a sensor support member provided on said temperature probe so as to substantially prevent gases in said gases compartment from escaping therefrom.

20. Apparatus as claimed in claim 18 wherein baffle means are provided in said gases compartment between said microporous wall and said at least one aperture to provide a tortuous path for gases which have passed over said microporous wall to allow humidification of said gases before said gases reach a temperature sensor provided on said temperature sensor support member.

21. Apparatus as claimed in claim 17 wherein a condensation removal means is also provided in a lowermost part of said gases passageway in an area adjacent to said liquid compartment where condensation in said gases passageways tends to collect in use.

22. Apparatus as claimed in claim 21 wherein said condensation removal means comprise a condensation removal aperture in said gases passageway, said aperture including a substance which is substantially permeable to liquid, but substantially impermeable to humidified gases such that condensation passes out of said gases passageway through said condensation removal aperture, but substantially no gases pass out of said gases passageway though said condensation removal aperture.

23. Apparatus as claimed in claim 22 wherein said condensation removal aperture has a condensation removal conduit attached thereto for removal of said condensation.

24. Apparatus as claimed in claim 17 wherein said inlet to said gases passageway is connected to an inspiratory line and an expiratory line of a gases breathing circuit so that said gases pass in divided form over said microporous wall in alternate direction alternating between a direction from said inlet to said outlet and a direction from said outlet to said inlet.

25. Apparatus as claimed in claim 16 wherein said gases passageway is provided with a second gases outlet, the construction and arrangement being such that said inlet and said second outlet are connected to an inspiratory and an expiratory line respectively of a gases breathing circuit.

26. Apparatus as claimed in claim 25 wherein said second outlet is provided in a lowermost part of said gases passageway in an area adjacent to said liquid compartment where condensation collects in use so that condensation in said gases passageway is drained therefrom by said second outlet.

27. Apparatus for humidifying gases, said apparatus comprising a liquid compartment, a liquid supply inlet through which liquid is in use supplied to said liquid compartment, a gases passageway through which gases are supplied to pass over a microporous wall common to both said liquid compartment and said gases passageway at a point of use, said microporous wall being permeable to vapour but substantially impermeable to liquid, heating means energisable to heat said liquid to generate vapour pressure within said liquid compartment sufficient to cause passage of vapour but not liquid through said microporous wall, a temperature probe having a temperature sensor said probe being adapted to be removably associated with said gases passageway in a manner such that said temperature sensor is positioned to sense the temperature of gases flowing in said gases passageway, said heating means or said apparatus having energy supply connector means for interconnection with heater connector means provided on said temperature probe for use with said apparatus, the construction and arrangement being such that only when said first temperature sensor is disposed within said gases passageway is said energy supply connection means interconnected with said heater connection means and energy supplied to said heating means.

28. Apparatus as claimed in claim 27 wherein a wall defining a sensor support member aperture is provided in said gases passageway for accommodating said sensor support member.

29. Apparatus as claimed in claim 27 or claim 28 wherein a surface of said wall is configured to make a sealing contact with a surface of a sensor support member provided on said temperature probe so as to substantially prevent gases in said gases passageway from escaping therefrom.

30. Apparatus as claimed in claim 27 wherein baffle means are provided in said gases passageway between said microporous wall and said at least one aperture to provide a tortuous path for gases which have passed over said microporous wall to allow humidification of said gases before said gases reach a temperature sensor provided on said temperature sensor support member.

31. Apparatus as claimed claim 27 wherein a condensation removal means is also provided in a lowermost part of said gases passageway in an area adjacent to said liquid compartment where condensation in said gases passageway tends to collect in use.

32. Apparatus as claimed in claim 31 said condensation removal means comprise a condensation removal aperture in said gases passageway, said aperture including a substance which is substantially permeable to liquid, but substantially impermeable to humidified gases such that condensation passes out of said gases passageway through said condensation removal aperture, but substantially no gases pass out of said gases passageway through said condensation removal aperture.

33. Apparatus as claimed in claim 32 wherein said condensation removal aperture has a condensation removal conduit attached thereto for removal of said condensation.

34. Apparatus as claimed in claim 27 wherein said inlet to said gases passageway is connected to an inspiratory line and an expiratory line of a gases breathing circuit so that said gases pass in divided form over said microporous wall in alternate directions alternating between a direction from said inlet to said outlet and a direction from said outlet to said inlet.

35. Apparatus as claimed in claim 27 wherein said gases passageway is provided with a second gases outlet, the construction and arrangement being such that said inlet and said second outlet are connected to an inspiratory and an expiratory line respectively of a gases breathing circuit.

36. Apparatus as claimed in claim 27 wherein said second outlet is provided in a lowermost part of said gases passageway in an area adjacent to said liquid compartment where condensation collects in use so that condensation in said gases passageway is drained therefrom by said second outlet.

37. A gases distribution passageway for providing a tortuous path for gases passing therethrough, said passageway comprising a gases body defining outer walls thereof, and a part of said walls defining an inlet conduit for gases to enter said passageway and a first outlet conduit for gases to exit said passageway, said passageway having support means therein for supporting a liquid body within said passageway with gases paths enabling gases to pass over and around said liquid body, said inlet conduit and said first outlet conduit being provided on opposite sides of said liquid body and substantially perpendicular to said liquid body such that gases enter said passageway through said inlet conduit in a direction substantially perpendicular to said liquid body and pass in divided form over and around said liquid body before exiting from said passageway through said first outlet conduit in a direction substantially perpendicular to said liquid body.

38. A gases distribution chamber as claimed in claim 37 wherein said liquid body comprises a substantially planar body.

39. A gases distribution chamber as claimed in claim 37 or claim 38 wherein said liquid body comprises a liquid compartment having a microporous wall, said microporous wall being permeable to vapour but substantially impermeable to liquid, said microporous wall comprising sheet microporous material formed into a liquid compartment of microporous material such that generation of vapour pressure within said liquid compartment causes passage of vapour but not liquid through said microporous wall to humidify said gases.

40. A gases distribution chamber as claimed in claim 38 wherein said substantially planar body comprises a baffle means of a substantially hydrophobic material.

41. A gases distribution chamber as claimed in claim 39 wherein said liquid compartment is substantially contained by said support means and said support means mechanically reinforce said liquid compartment of microporous material to resist the pressures operating thereon.

42. A gases distribution chamber as claimed in claim 39 said support means also provide flow directing means for direction the flow of said gases over said liquid compartment of microporous material to provide a tortuous path for gases to enter said apparatus and pass in divided form over said microporous wall for delivery from said apparatus.

43. A gases distribution chamber as claimed in claim 39 wherein said liquid compartment includes heating means to heat liquid in said liquid compartment to generate vapour pressure within said compartment.

44. A gases distribution chamber as claimed in claim 43 wherein said heating means include energy supply connector means for interconnection with heater connector means provided on a temperature probe for use with said apparatus.

45. A gases distribution chamber as claimed in claim 39 wherein said inlet conduit is connected to both an inspiratory line and an expiratory line of a gases breathing circuit so that said gases pass in divided form over said microporous wall in alternate directions alternating between a direction from said inlet conduit to said outlet conduit and a direction from said outlet conduit to said inlet conduit.

46. A gases distribution chamber as claimed in claim 37 wherein a second gases outlet conduit is provided, the construction and arrangement being such that said inlet conduit and said second outlet conduit are connected to an inspiratory and an expiratory line respectively of a gases breathing circuit.

47. A gases distribution chamber as claimed in claim 46 wherein said second outlet conduit is provided in a lowermost part of said chamber in an area adjacent to said liquid compartment where condensation collects in use so that condensation in said passageway is drained therefrom by said second outlet conduit.

48. A gases distribution chamber as claimed in claim 27 wherein a wall defining a sensor support member aperture is provided in said outer walls for accommodating a sensor support member.

49. A gases distribution chamber as claimed in claim 48 wherein a surface of said outer wall is configured to make a sealing contact with a surface of said sensor support member so as to substantially prevent gases in said chamber from escaping therefrom.

50. A gases distribution chamber as claimed in claim 37 wherein a condensation removal means is also provided in a lowermost part of said chamber in an area adjacent to said liquid compartment where condensation in said chamber tends to collect in use.

51. A gases distribution chamber as claimed in claim 50 wherein said condensation removal means comprise a condensation removal aperture in said chamber, said aperture including a substance which is substantially permeable to liquid, but substantially impermeable to gases such that condensation passes out of said chamber through said condensation removal aperture, but substantially no gases pass out of said chamber through said condensation removal aperture.

52. A gases distribution chamber as claimed in claim 51 wherein said condensation removal aperture has a condensation removal conduit attached thereto for removal of said condensation.

53. A gases distribution chamber as claimed in claim 37 wherein said first outlet conduit has a protruding edge provided adjacent thereto, said protruding edge providing a barrier to resist condensate in said chamber from entering said first outlet conduit.

* * * * *